United States Patent [19]

Ueda et al.

[11] 4,303,667
[45] Dec. 1, 1981

[54] PHENYLPRROLE DERIVATIVES

[75] Inventors: Akiyoshi Ueda, Hiratsuka; Shigeru Kojima, Odawara; Yasushi Yasuda, Yokohama; Hiroaki Nishikawa, Oisomachi; Akira Nakada, Shizuoka, all of Japan

[73] Assignee: Nippon Soda Company Limited, Tokyo, Japan

[21] Appl. No.: 138,502

[22] Filed: Apr. 9, 1980

[30] Foreign Application Priority Data

May 25, 1979 [JP] Japan .................................. 54-64793
Jun. 4, 1979 [JP] Japan .................................. 54-69570
Jul. 25, 1979 [JP] Japan .................................. 54-94728

[51] Int. Cl.³ ............................................. C07D 207/30
[52] U.S. Cl. ........................................ 424/274; 71/95;
260/313.1; 260/326.4
[58] Field of Search ...................... 260/326.4; 424/274

[56] References Cited

U.S. PATENT DOCUMENTS 3,083,208 3/1963 Wu et al. ........................... 260/326.4
3,644,414 2/1972 Helsley et al. ................... 260/326.4
4,234,484 11/1980 Mitzlaff et al. ................... 260/326.4

FOREIGN PATENT DOCUMENTS 709847 5/1965 Canada .............................. 260/326.4

OTHER PUBLICATIONS

Vanbreuseghem, et al., "Chemical Abstracts", vol. 88, 1978, col. 88:69672e.
Karime, et al., "Chemical Abstracts," vol. 88, 1978, col. 88:165,487u.
Okuma, et al., "Chemical Abstracts," vol. 91, 1979, col. 91:152742k.
Ueda, et al., "Chemical Abstracts," vol. 91, 1979, col. 91:175184u.

Primary Examiner—Donald G. Daus
Assistant Examiner—James H. Turnipseed
Attorney, Agent, or Firm—George B. Oujevolk

[57] ABSTRACT

Compounds of the general formula

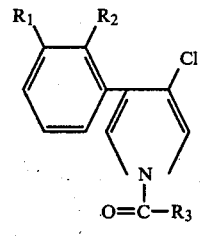

wherein $R_1$ is hydrogen or chlorine,
$R_2$ is hydrogen, chlorine or nitro, and
$R_3$ is hydrogen or methoxymethyl, with the proviso that
  $R_1$ and $R_2$ do not represent hydrogen simultaneously,
are outstanding effective fungicides.

15 Claims, No Drawings

PHENYLPRROLE DERIVATIVES

DETAILED DESCRIPTION OF THE INVENTION

The present invention relates to novel phenylpyrrole derivatives, to a process for the preparation thereof and their uses as fungicides, in particular to fungicidally active compositions and method for controlling fungi.

It is already known that various phenylpyrroles, for example, 3-chloro-4-(2-nitro-3-chlorophenyl)pyrrole (U.S. Pat. No. 3,428,648) and 3-chloro-4-(3,4-dichlorophenyl)pyrrole (U.K. Pat. No. 1,125,169) have antibiotic activity and are useful as medicines.

However, these known phenylpyrroles can not be used in agricultural application because the compounds are unstable against sunlight and their residual effects are low.

The inventors have studied the fungicidal activity of various 3-phenylpyrroles and have found that the phenylpyrroles of the formula [I]

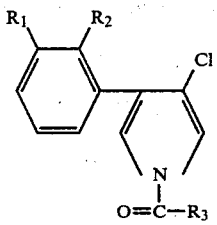

wherein $R_1$ is hydrogen or chlorine,
$R_2$ is hydrogen, chlorine or nitro, and
$R_3$ is hydrogen or methoxymethyl, with the proviso that $R_1$ and $R_2$ do not represent hydrogen simultaneously,
have outstandingly superior fungicidal effect in agricultural application to the known phenylpyrroles.

In the compounds of formula [I], the compounds where $R_1$ and $R_2$ are chlorine are preferable as fungicide for agricultural application.

The compounds of this invention can be prepared by the conventional acylation reaction of the compounds of the formula [II]

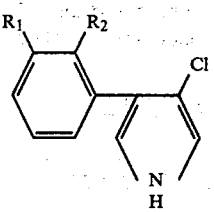

namely, by the reaction of the compounds of the formula [III]

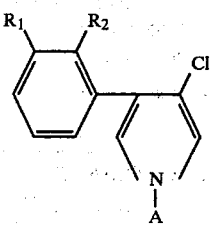

(A is hydrogen, alkali metal or the other reactive groups such as silyl groups.) with an acylating agent such as methoxyacetyl halides, methoxyacetic anhydride, 1-methoxyacetyl imidazole or 1-formyl imidazole.

Typical compounds of this invention are shown in Table I.

TABLE 1

| Compound No. | Chemical Structure | | | Physical Constant (m.p.: °C.) |
|---|---|---|---|---|
| | $R_1$ | $R_2$ | $R_3$ | |
| 1 | Cl | Cl | $CH_2OCH_3$ | 87–88 |
| 2 | Cl | $NO_2$ | $CH_2OCH_3$ | 129–130 |
| 3 | H | Cl | $CH_2OCH_3$ | 71.5–72 |
| 4 | Cl | H | $CH_2OCH_3$ | 76.5–78.5 |
| 5 | Cl | Cl | H | 130.5–130.75 |
| 6 | Cl | $NO_2$ | H | 137.5–138.5 |
| 7 | H | Cl | H | 72.5–74 |
| 8 | Cl | H | H | 63–65 |

The following examples illustrate the preparation of compounds according to the invention:

EXAMPLE 1

3-chloro-4-(2,3-dichlorophenyl)-1-methoxyacetylpyrrole (Compound No. 1)

10 ml of a solution of 2.9 g of sodium salt of 3-chloro-4-(2,3-dichloropheny) pyrrole in tetrahydrofuran was added dropwise to a solution of 1.9 g of methoxyacetyl chloride in 10 ml of tetrahydrofuran at room temperature under nitrogen atmosphere with stirring. The stirring was continued for 3.5 hours at room temperature and then the solvent was removed by distillation under reduced pressure. The residue was purified by column chromatography on silica gel to obtain 2.3 g of the desired compound as colorless crystals.
m.p. 87°–88° C.

EXAMPLE 2

3-chloro-4-(3-chloro-2-nitrophenyl)-1-methoxyacetylpyrrole (Compound No. 2)

0.2 g of small pieces of potassium were added to a solution of 1.3 g of 3-chloro-4-(3-chloro-2-nitrophenyl)-pyrrole in 20 ml of tetrahydrofuran with stirring under nitrogen atmosphere. The solution was refluxed for one hour and cooled to room temperature. To the solution was added dropwise 10 ml of solution of 2.71 g of methoxyacetylchloride in tetrahydrofuran with stirring. The stirring was continued for one hour at room temperature and then, the solvent was removed by distillation under reduced pressure. The residue was purified by column chromatography on silica gel. The resulting crude crystals were further purified by washing with ether to obtain 0.6 g of the desired compound.
m.p. 129°–130° C.

EXAMPLE 3

3-chloro-4-(3-chlorophenyl)-1-methoxyacetyl pyrrole (Compound No. 4)

0.4 g of potassium was added to a solution of 1.8 g of 3-chloro-4-(3-chlorophenyl)pyrrole in 20 ml of tetrahydrofuran and the solution was refluxed for 2 hours. The reaction solution was cooled to room temperature and was added dropwise to a solution of 4.6 g methoxyacetyl chloride in 20 ml of tetrahydrofuran. The solution was stirred for three hours at room temperature and left overnight. After the removal of the solvent by distillation under reduced pressure, the residue was dissolved in ethyl acetate, and the solution was washed with water and dried with anhydrous magnesium sulfate. The solvent was removed by distillation and the residue was purified by column chromatography on silica gel to obtain 0.8 g of the desired compound.

m.p. 76.5°–78.5° C.

EXAMPLE 4

3-chloro-4-(2,3-dichlorophenyl)-1-methoxyacetyl pyrrole (Compound No. 1)

11 g of triethylamine was added to a solution of 12 g of 3-chloro-4-(2,3-dichlorophenyl)pyrrole in 200 ml of benzene with stirring. To the solution was added dropwise a solution of 16 g of methoxyacetic anhydride in 200 ml of benzene and the resulting solution was stirred for 64 hours at room temperature. 100 ml of benzene was added to the reaction solution and washed subsequently with water, aqueous solution of sodium bicarbonate and then saturated aqueous solution of sodium chloride. The solution was dried with anhydrous magnesium sulfate and then the solvent was removed by distillation under reduced pressure. The residue was extracted with heated hexane and the extract was cooled to obtain 13.85 g of the desired compound.

EXAMPLE 5

3-chloro-4(2,3-dichlorophenyl)-1-formylpyrrole (Compound No. 5)

5 ml of a solution of 0.7 g of formic acid (99%) in tetrahydrofuran was added dropwise to a solution of 2.3 g of carbodiimidazole in 50 ml of tetrahydrofuran at room temperature with stirring to prepare the solution of 1-formylimidazole. A solution of 1g of 3-chloro-4-(2,3-dichlorophenyl) pyrrole in 10 ml of tetrahydrofuran was added dropwise to the solution of 1-formylimidazole. After refluxing the solution for two hours with stirring, the resulting reaction solution was left overnight and then the solvent was removed by distillation under reduced pressure. The residue was dissolved in 100 ml of ethyl acetate and the solution was washed with water and then saturated aqueous solution of sodium chloride. After drying the solution with anhydrous magnesium sulfate, the solvent was removed by distillation to obtain 1.1 g of the desired product. The product was purified by recrystallization from ethyl acetate to obtain colorless needles of the desired compound.

m.p. 130.5°–130.75° C.

EXAMPLE 6

3-chloro-4-(2-nitro-3-chlorophenyl)-1-formylpyrrole (Compound No. 6)

1 g of 3-chloro-4-(2-nitro-3-chlorophenyl)pyrrole was reacted and treated in the same way as in Example 5 to obtain 200 mg of the desired compound as colorless crystals.

m.p. 137.5°–138.5° C.

The compounds of the invention possess excellent fungicidal activity when employed to prevent damage to plants, in particular, the compounds possess outstanding residual activity.

The compound may be used directly without mixing with carriers.

The active ingredient of a fungicidal composition according to the invention may be formulated by mixing with suitable carriers in a form generally used in pesticidal compositions, such as wettable powder, emulsifiable concentrate, dust formulation and granular formulation. As solid carriers, bentonite, diatomaceous earth, apatite, gypsum, talc, pyrophyllite, vermiculite and clay, for example, may be used. As liquid carriers, kerosene, mineral oil, petroleum, solvent naphtha, xylene, cyclohexane, cyclohexanone, dimethylformamide, dimethylsulfoxide, alcohol, acetone, benzene and water, for example, may be used. If so desired, a surface active agent may be added in order to give a homogeneous and stable formulation.

The concentration of the active ingredient in the fungicidal composition may vary according to type of formulation, and is for example, 5 to 80 weight percent, preferably 20 to 80 weight percent, in wettable powder; 5 to 70 weight percent, preferably 10 to 50 weight percent, in emulsifiable concentrate; and 0.5 to 20 weight percent, preferable 1 to 10 weight percent, in dust formulation or in granular formulation.

Furthermore, the compounds may be used in mixture with other fungicides, insecticides, acaricides and herbicides.

Some non-limiting examples of fungicidal compositions according to the invention are as follows:

EXAMPLE 7

| Wettable Powder | |
|---|---|
| | Parts by weight |
| Compound No. 1 | 20 |
| Diatomaceous earth | 73 |
| Sodium higheralkyl sulfate | 7 |

These compounds were mixed homogeneously and reduced to fine particles to provide a wettable powder containing 20% of the active ingredient.

EXAMPLE 8

| Emulsifiable Concentrate | |
|---|---|
| | Parts by weight |
| Compound No. 2 | 20 |
| Xylene | 42 |
| Dimethylformamide | 30 |
| Polyoxyethylene alkylphenyl ether | 8 |

These ingredients were mixed and dissolved to provide an emulsifiable concentrate containing 20% of the active ingredient.

EXAMPLE 9

| Dust Formulation | |
|---|---|
| | Parts by weight |
| Compound No. 5 | 2 |
| Talc | 98 |

These ingredients were mixed homogeneously and reduced to fine particles to provide a dust formulation containing 2% of the active ingredient.

EXAMPLE 10

| Granular Formulation | |
|---|---|
| | Parts by weight |
| Compound No. 6 | 5 |
| Talc | 40 |

| Granular Formulation | |
|---|---|
| | Parts by weight |
| Clay | 39 |
| Bentonite | 10 |
| Sodium alkylsulfate | 6 |

These were mixed homogeneously and reduced to fine particles. The fine particles were made into granules, each having a diameter in the range of 0.5 1 mm, to provide a granular formulation containing 5% of the active ingredient.

The wettable powder or the emulsifiable concentrate is diluted with water to a desired concentration and used as a suspension or emulsion for treating soil, plant or seed. The dust formulation or the granular formulation is directly used for treating soil, plant or seed.

The fungicides of the present invention are effective for the control of many plant diseases, for example, by applying the fungicides to plants, gray mold and Schlerotinia rot of vegetables, leaf mold of tomato, anthracnose, Fusarium wilt and gummy stem blight of cucumber, blast, sheath blight and Helminthosporium leaf spot of rice, stripe of barley, black spot of pear, brown rot of peach, gray mold of grape and scab of apple can be controlled. By treating soil, anthracnose, Fusarium wilt and gummy stem blight of cucumber can be controlled. By treating seeds, blast and Helminthosporium leaf spot of rice, bunt of wheat and stripe of barley can be controlled.

The fungicidal effect of the compounds of this invention is illustrated by the following tests:

Test 1. Test for control of Gray Mold of Bean

Detached leaves of kidney beans (*Phaseolus vulgaris*) were immersed for about 30 seconds in aqueous suspensions prepared by diluting a wettable powder to the concentration of 25 ppm of test compound. After air drying, the treated leaves were inoculated with mycelia of *Botrytis cinerea* and kept at 20° C. in a moist chamber. Control effect was determined 4 days after inoculation. The results are shown in Table 2. Phyto-toxicity was not observed.

TABLE 2

| | Control Value (%) |
|---|---|
| Test Compound No. | |
| 1 | 100 |
| 2 | 100 |
| 3 | 100 |
| 4 | 100 |
| 5 | 100 |
| 6 | 100 |
| 7 | 100 |
| 8 | 100 |
| Comparative Compound* | |
| 1 | 100 |
| 2 | 48 |

*Comparative Compound
1. 3-chloro-4-(2-nitro-3-chlorophenyl)pyrrole (U.S.P. 3,428,648)
2. Euparen (Trade name): N'-dichlorofluoromethylthio-N,N-dimethyl-N'-phenyl-sulfamide Test 2. Test for Control of Gray Mold of Bean (residual effect)

Potted kidney bean (*Phaseolus vulgaris* L.) seedlings which was grown for about 3 weeks were sprayed once with a suspension of a test compound prepared by diluting a wettable powder with water, and kept in a greenhouse. The leaves were detached and inoculated with mycelia of *Botrytis cinerea* 7 days after spraying and kept in a moist chamber at 20° C. Control effect was determined 4 days after the inoculation.

The results are shown in Table 3. Phyto-toxicity was not observed.

TABLE 3

| | Concentration of the Active ingredient (ppm) | Control Value (%) |
|---|---|---|
| Test compound No. | | |
| 1 | 25 | 100 |
| 2 | " | 100 |
| 3 | " | 100 |
| 4 | " | 100 |
| 5 | " | 100 |
| 6 | " | 100 |
| 7 | " | 100 |
| 8 | " | 100 |
| Comparative Compound* | | |
| 1 | 200 | 0 |
| 2 | " | 58 |
| 3 | " | 0 |
| 4 | " | 79 |

*Test Compound
1 and 2: the same as in Table 2
3: 3-chloro-4-(3,4-dichlorophenyl)pyrrole (U.K. Patent No. 1,125,169)
4: Rovral (Trade name): 1-isopropylcarbamoyl-3-(3,5-dichlorophenyl)hydantoin Test 3. Test for Control of Helminthosporium Leaf Spot of Rice by Seed-treatment Rice seeds infected with *Helminthosporium oryzae* were dipped for 24 hours in a suspension of a test compound which was prepared by diluting the wettable powder containing the test compound to a given concentration. The seeds were airdried and then soaked with water. After treatment for hastening of germination, the treated seeds were sowed in the sand and cultivated in a green house. Control effect was determined 2 weeks after sowing. The results are shown in Table 4.

TABLE 4

| Compound No. | Concentration of the Active Ingredient (ppm) | Control Value (%) |
|---|---|---|
| 1 | 100 | 96 |
| | 50 | 94 |
| | 25 | 93 |
| 5 | 100 | 94 |
| | 50 | 93 |
| | 25 | 91 |
| Untreated | — | 0 |
| Thiram* | 500 | 66 |

*Thiram (Trade name): Tetramethylthiuram disulfide

We claim:
1. A compound of the general formula

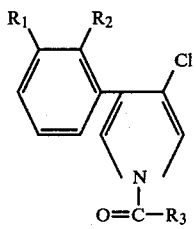

wherein
- $R_1$ is hydrogen or chlorine
- $R_2$ is hydrogen, chlorine or nitro, and
- $R_3$ is hydrogen or methoxymethyl, with the proviso that $R_1$ and $R_2$ do not represent hydrogen simultaneously.

2. A compound according to claim 1, wherein $R_3$ is methoxymethyl.

3. A compound according to claim 1, wherein $R_3$ is hydrogen.

4. A compound according to claim 1, wherein $R_1$ is chlorine and $R_2$ is chlorine or nitro.

5. A compound according to claim 4, wherein $R_1$ and $R_2$ are chlorine.

6. A fungicidal composition comprising an inert carrier and a fungicidally effective amount of a compound of claim 1.

7. A fungicidal composition comprising an inert carrier and a fungicidally effective amount of a compound of claim 2.

8. A fungicidal composition comprising an inert carrier and a fungicidally effective amount of a compound of claim 3.

9. A fungicidal composition comprising an inert carrier and a fungicidally effective amount of a compound of claim 4.

10. A fungicidal composition comprising an inert carrier and a fungicidally effective amount of a compound of claim 5.

11. A method for the control of fungi comprising applying to the locus to be protected an effective amount of a compound of claim 1.

12. A method for the control of fungi comprising applying to the locus to be protected an effective amount of a compound of claim 2.

13. A method for the control of fungi comprising applying to the locus to be protected an effective amount of a compound of claim 3.

14. A method for the control of fungi comprising applying to the locus to be protected an effective amount of a compound of claim 4.

15. A method for the control of fungi comprising applying to the locus to be protected an effective amount of a compound of claim 5.

* * * * *